United States Patent
Pathi et al.

(10) Patent No.: US 7,989,636 B2
(45) Date of Patent: Aug. 2, 2011

(54) PROCESS FOR THE PREPARATION OF PURE ANASTROZOLE

(75) Inventors: Srinivas Laxminarayan Pathi, Bangalore (IN); Rajendra Narayanrao Kankan, Mumbai (IN); Dharmaraj Ramachandra Rao, Thane (IN)

(73) Assignee: Cipla Limited, Mumbai (IN)

( * ) Notice: Subject to any disclaimer, the term of this patent is extended or adjusted under 35 U.S.C. 154(b) by 24 days.

(21) Appl. No.: 12/444,613

(22) PCT Filed: Oct. 17, 2007

(86) PCT No.: PCT/GB2007/003942
§ 371 (c)(1),
(2), (4) Date: Apr. 7, 2009

(87) PCT Pub. No.: WO2008/047104
PCT Pub. Date: Apr. 24, 2008

(65) Prior Publication Data
US 2010/0099887 A1    Apr. 22, 2010

(30) Foreign Application Priority Data
Oct. 17, 2006   (IN) .................. 1719/MUM/2006

(51) Int. Cl.
*C07D 249/08*  (2006.01)
(52) U.S. Cl. .................................. 548/262.2
(58) Field of Classification Search .......... None
See application file for complete search history.

(56) References Cited

U.S. PATENT DOCUMENTS

| 4,935,437 | A | 6/1990 | Edwards et al. |
| RE36,617 | E | 3/2000 | Edwards et al. |
| 7,692,025 | B2 * | 4/2010 | Villa et al. ............ 548/262.2 |
| 2006/0035950 | A1 | 2/2006 | Alnabari et al. |
| 2006/0189670 | A1 | 8/2006 | Khile et al. |

FOREIGN PATENT DOCUMENTS

| EP | 1705168 A1 | 9/2006 |
| WO | 2006108155 A2 | 10/2006 |
| WO | 2007105231 A1 | 9/2007 |
| WO | 2008047104 A1 | 4/2008 |

OTHER PUBLICATIONS

Foreign communication from the priority application—International Search Report and Written Opinion, PCT/GB2007/003942, Jan. 31, 2008, 12 pages.
Foreign communication from the priority application—International Preliminary Report on Patentability, PCT/GB2007/003942, Apr. 22, 2009, 6 pages.

* cited by examiner

*Primary Examiner* — Kamal Saeed
*Assistant Examiner* — Nyeemah A Grazier
(74) *Attorney, Agent, or Firm* — Conley Rose, P.C.; Rodney B. Carroll

(57) ABSTRACT

A process for the preparation of anastrozole which comprises: a) brominating 3,5-bis(2-cyanoprop-2-yl)toluene (II) in an organic solvent using a brominating agent to obtain 3,5-bis(2-cyanoprop-2-yl)benzylbromide (III); b) heating the reaction mass of step a) to the reflux temperature of the organic solvent for a period of time no longer than 3 hours; c) isolating and purifying the bromo intermediate (III) using an organic solvent; d) alkylating the bromo intermediate in the presence of a base, optionally a phase transfer catalyst, a 1,2,4-triazole and an organic solvent to obtain anastrozole; and e) isolating and purifying the anastrozole from an organic solvent.

29 Claims, No Drawings

PROCESS FOR THE PREPARATION OF PURE ANASTROZOLE

CROSS-REFERENCE TO RELATED APPLICATIONS

This application is a filing under 35 U.S.C. 371 of International Application No. PCT/GB2007/003942 filed Oct. 17, 2007, entitled "Process for the Preparation of Pure Anastrozole," claiming priority of Indian Patent Application No. 1719/MUM/2006 filed Oct. 17, 2006, which applications are incorporated by reference herein in their entirety.

FIELD OF THE INVENTION

The present invention relates to an improved process for preparing pure anastrozole. Moreover the process relates to alkylation of the isolated and purified 3,5-bis(2-cyanoprop-2-yl)benzylbromide as starting material, without the use of toxic, hazardous and environmentally unfriendly solvents.

BACKGROUND OF THE INVENTION

Anastrozole is a common name for the chemically known substance 2,2'-[5-(1H-1,2,4-triazol-1-ylmethyl)-1,3-phenylene]di(2-methylpropionitrile), represented by formula (I):

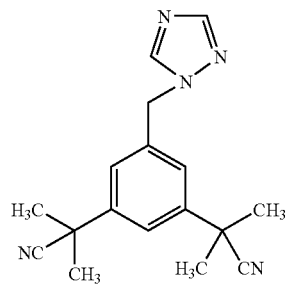

I

Anastrozole is a selective and potent non-steroidal drug which inhibits the action of the enzyme aromatase. It is used for the treatment of advanced breast cancer in postmenopausal women with disease progression following tamoxifen therapy. Anastrozole is further recognized and granted for treatment of postmenopausal women with hormone receptor positive or hormone receptor unknown, locally advanced or metastatic breast cancer and also for adjuvant treatment of postmenopausal women with hormone receptor positive early breast cancer.

The synthesis of anastrozole is described in U.S. Pat. Nos. 4,935,437 and RE 36617 (a re-issue of U.S. Pat. No. 4,935,437 assigned to AstraZeneca Pharmaceuticals). These patents describe two synthetic routes for preparing anastrozole, one starting from methyl-3,5-dimethylbenzoate in a six-step process and the other started from 3,5-bis(bromomethyl)toluene in a three-step process. The second process is preferable because it is much shorter and easier to perform, however both processes involve a benzylic bromination stage with N-bromosuccinimide (NBS) in $CCl_4$.

In the first process, bromination of methyl-3,5-dimethylbenzoate with N-bromosuccinimide (NBS) in $CCl_4$ affords a 3,5-bis(bromomethyl) compound, which is subsequently treated with potassium cyanide to afford a dinitrile compound. The dinitrile compound is alkylated, then reduced to the corresponding alcohol. The alcohol is converted to an alkyl chloride intermediate, and anastrozole is then obtained by reaction of the latter compound with sodium triazole. The final product is purified by flash column chromatography, using a repeated elution with a methanol:chloroform solvent mixture.

In the second process, the starting material, 3,5-bis(bromomethyl)-toluene, is reacted with potassium cyanide in dichloromethane in the presence of a catalytic amount of tetrabutylammonium bromide (TBAB) to obtain 2,2'-(5-methyl-1,3-phenylene)diacetonitrile. The product is mixed with iodomethane and sodium hydride in DMF to thereby obtain 2,2'-(5-methyl-1,3-phenylene)di(2-methylpropionitrile), (also referred to as 3,5-bis(2-cyanoprop-2-yl)toluene) which is further brominated using benzoyl peroxide and N-bromosuccinimide (NBS) in carbon tetrachloride. The mixture is refluxed for 2 hours, cooled, filtered, and the filtrate is evaporated to dryness under reduced pressure. The residue obtained is dissolved in DMF and sodium triazole is added. After completion of the reaction, anastrozole is purified by flash column chromatography, eluting with ethyl acetate. The last part of this process is shown in Scheme 1 below.

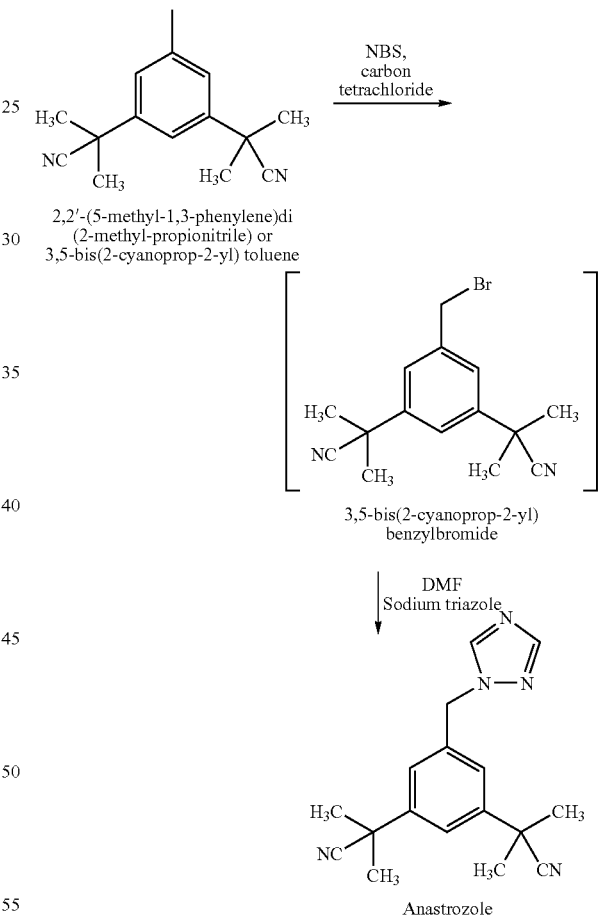

Thus, the bromomethyl intermediate in the process is not isolated or purified in either process, but is directly converted to anastrozole in situ. As a result of using the non-isolated, non-purified intermediate, an impure final product is obtained.

Further, the use of a chromatographic solvent such as chloroform (being a carcinogenic solvent), the use of a solvent such as carbon tetrachloride (also being a carcinogenic solvent) for the bromination reaction, and DMF for the alkylation reaction is disadvantageous with respect to industrial application.

US 20060189670 describes the preparation of anastrazole by reacting 3,5 bis-(1-cyano-1 methyl ethyl)benzylhalide with 4-Z-1,2,4-triazole.

US 2006/0035950 provides processes (scheme II) for purifying anastrozole, avoiding the use of liquid chromatography. The purification processes are via the isolated anastrozole salt forms, either by crystallization or by selective acidic extractions, and optionally in both cases, converting the purified anastrozole salt to anastrozole base. A process for the synthesis of anastrozole, which is obtained by alkylating the isolated, purified, 3,5-bis(2-cyanoprop-2-yl)benzylbromide is also disclosed.

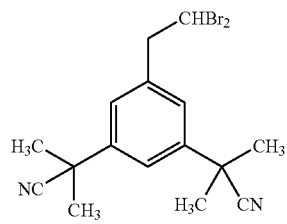

IV

Scheme II

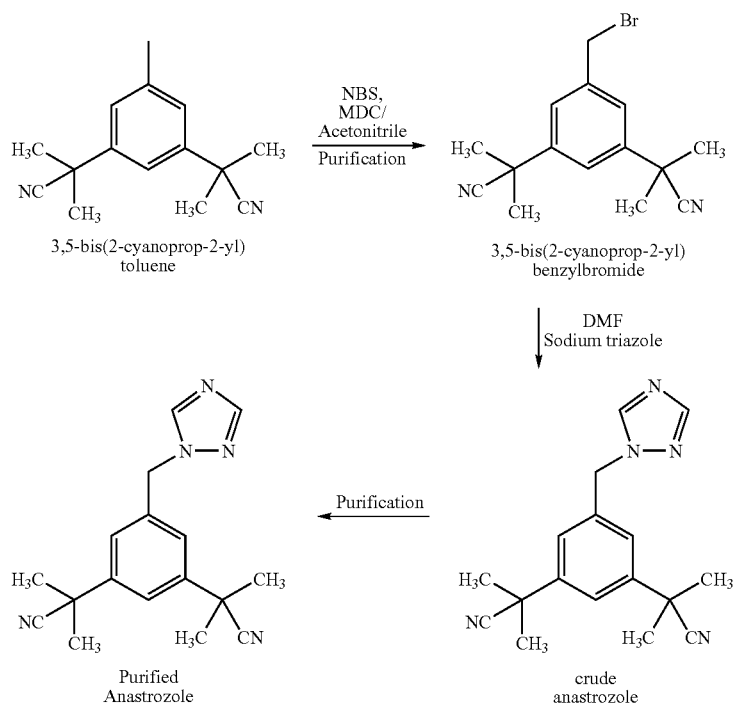

The above patent describes the preparation of 3,5-bis(2-cyanoprop-2-yl)benzylbromide, which is carried out in a solvent of either dichloromethane (the yield is low), or acetonitrile (the yield is not reported) and purified (the yield reported in this process is low). There are a number of steps involved in the synthesis of anastrozole, resulting in lower yield. For example, following alkylation to produce crude anastrozole, the US'950 process involves converting the crude anastrozole to a salt of anastrozole, isolating the salt of anastrozole, optionally recrystallising the salt of anastrozole, optionally converting the salt of anastrozole to anastrozole base and isolating the product.

The bromination reaction as described in U.S. Pat. No. '950 can be carried out in a solvent selected from the group of ethyl acetate, acetone, dichloromethane, methyl acetate, isopropyl acetate, isopropyl acetoacetate, tert-butyl acetate and acetonitrile. However, it was found that in the presence of some solvents, the purity of the product was not high. The impurity 3,5-bis(cyanoprop-2-yl)benzyl bromide, a compound of formula (IV) formed during the reaction was found to an extent of 15-20% and other problems were encountered using some of these solvents which are susceptible to bromination.

The bromination reaction described in U.S. Pat. No. '950 was followed by reflux for 4-5 hours. The U.S. Pat. No. '950 inventors have found that longer reaction times cause increased levels of the impurity 3,5-bis(cyanoprop-2-yl)benzylbromide. Thus, the bromination process described in US2006/0035950 is not an efficient process to produce the product in high yield. Furthermore, the purification of the crude anastrozole involves many steps, which makes the process less suitable for industrial application and reduces yield.

Because of the difficulties encountered in the process disclosed in the prior art, for example using carbon tetrachloride ($CCl_4$) and DMF on an industrial scale, and the lower yields, it would be highly desirable to develop a process for preparing anastrozole, which does not involve the use of carcinogenic solvents like carbon tetrachloride and DMF and which results in a high yield, high purity product.

Anastrozole is administered in a 1 mg dosage and it is a very expensive product. Thus, there is a constant need for developing a new process for its preparation, which provides good yield with high purity, making the process commercially viable. The process of the present invention provides anastrozole in good yield with high purity.

SUMMARY OF THE INVENTION

The main object of the present invention is to provide an improved process for preparation of anastrazole with purity greater than 99.8%.

The present invention provides a process for the preparation of anastrozole which comprises:

a) brominating 3,5-bis(2-cyanoprop-2-yl)toluene (II) in an organic solvent using a brominating agent to obtain 3,5-bis(2-cyanoprop-2-yl)benzylbromide (III);

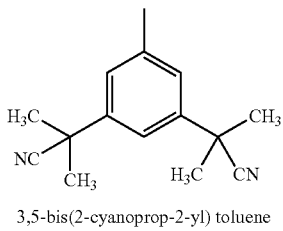

3,5-bis(2-cyanoprop-2-yl) toluene

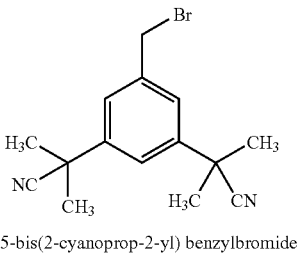

3,5-bis(2-cyanoprop-2-yl) benzylbromide b) isolating and purifying the bromo intermediate (III) using an organic solvent;

c) alkylating the bromo intermediate in the presence of a base, optionally a phase transfer catalyst, a 1,2,4-triazole and an organic solvent to obtain anastrozole; and

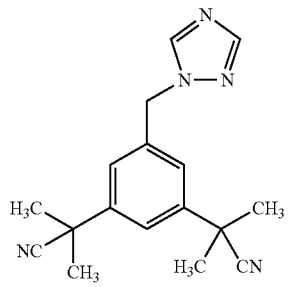

d) isolating and purifying the anastrozole from an organic solvent.

Preferably, the bromination reaction of step a) is carried out at the reflux temperature of the solvent used in step a). It has surprisingly been found that carrying out the refluxing for a period of time not longer than 3 hours reduces the formation of the impurity 3,5-bis(cyanoprop-2-yl)benzyl bromide (IV)

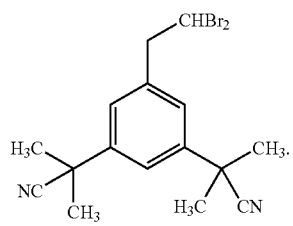

Thus, according to another aspect of the present invention, there is provided a process for the preparation of anastrozole which comprises: a) brominating 3,5-bis(2-cyanoprop-2-yl) toluene (II) in an organic solvent using a brominating agent to obtain 3,5-bis(2-cyanoprop-2-yl)benzylbromide (III); b) heating the reaction mass of step a) to the reflux temperature of the organic solvent for a period of time no longer than 3 hours; c) isolating and purifying the bromo intermediate (III) using an organic solvent; d) alkylating the bromo intermediate in the presence of a base, optionally a phase transfer catalyst, a 1,2,4-triazole and an organic solvent to obtain anastrozole; e) isolating and purifying the anastrozole from an organic solvent. Preferably, the organic solvent in the brominating step is acetonitrile.

There is also provided by the present invention a process for preparing 3,5-bis(2-cyanoprop-2-yl)benzylbromide (III) which comprises brominating 3,5-bis(2-cyanoprop-2-yl) toluene (II) in an organic solvent using a brominating agent, heating the reaction mass to the reflux temperature of the organic solvent for a period of time no longer than 3 hours; and isolating and purifying the bromo intermediate (III) using an organic solvent to obtain 3,5-bis(2-cyanoprop-2-yl)benzylbromide (III). Preferably, the organic solvent in the brominating step is acetonitrile.

Suitably, the refluxing is carried out for 3 hours. Preferably, the refluxing is carried out for 1 hour.

The preferred the organic solvent for use in step a) is acetonitrile. It has surprisingly been found that using acetonitrile as the bromination solvent is particularly effective in aiding the removal of the impurity (IV).

Thus, according to another aspect of the present invention, there is provided a process for the preparation of anastrozole which comprises: a) brominating 3,5-bis(2-cyanoprop-2-yl) toluene (II) in acetonitrile using a brominating agent to obtain 3,5-bis(2-cyanoprop-2-yl)benzylbromide (III); b) isolating and purifying the bromo intermediate (III) using an organic solvent; c) alkylating the bromo intermediate in the presence of a base, optionally a phase transfer catalyst, a 1,2,4-triazole and an organic solvent to obtain anastrozole; and d) isolating and purifying the anastrozole from an organic solvent. Preferably, the bromination reaction mass is heated to the reflux temperature of the organic solvent for a period of time no longer than 3 hours.

There is also provided by the present invention a process for preparing 3,5-bis(2-cyanoprop-2-yl)benzylbromide (III) which comprises brominating 3,5-bis(2-cyanoprop-2-yl) toluene (II) in acetonitrile using a brominating agent, and isolating and purifying the bromo intermediate (III) using an organic solvent to obtain 3,5-bis(2-cyanoprop-2-yl)benzylbromide (III). Preferably, the bromination reaction mass is heated to the reflux temperature of acetonitrile for a period of time no longer than 3 hours.

Using acetonitrile as the organic solvent in the brominating step and employing the step of heating the bromination reaction mass to the reflux temperature of the organic solvent for a period of time no longer than 3 hours is particularly preferred.

The brominating agent may be an N-halosuccinimide. Preferably, the N-halosuccinimide is N-bromosuccinimide.

The organic solvent used in the purification of the brominated intermediate may be selected from the group consisting of isopropyl alcohol, n-heptane, n-hexane, toluene and mixtures thereof. Preferably, the organic solvent is a mixture of isopropyl alcohol and n-heptane.

The isolation of the brominated intermediate may involve quenching the reaction mass with water, concentrating the quenched reaction mass to a residue, charging an organic solvent such as methylene chloride to the residue, filtering the insolubles and washing with the solvent. The organic layer may be washed with a sodium sulfite solution, followed by a sodium chloride solution then a sodium chloride solution. The layer may then be washed with water, dried and concentrated to a residue.

The base used in the alkylating step may be selected from the group consisting of potassium carbonate, sodium carbonate, sodium hydroxide, potassium hydroxide, sodium bicarbonate, potassium bicarbonate and mixtures thereof. Preferably, the base is potassium carbonate and potassium hydroxide, and the potassium hydroxide is in powdered form.

The phase transfer catalyst may be a quaternary ammonium salt for example a tetraalkyl ammonium halide, or a crown ether. The alkyl group is an alkyl of 1 to 18 carbon atoms. Preferably, the alkyl is methyl, ethyl or propyl. The halide may be chloro, bromo or iodo. For example, the tetraalkyl ammonium halide may be $Me_4NCl$, $Me_4NBr$, $Me_4NI$, $Et_4NBr$, $n-Pr_4NCl$, $n-Pr_4NI$ or $n-Bu_4NBr$. Suitably, the tetraalkyl ammonium halide is tetrabutylammonium bromide.

The organic solvent used in the alkylating step may be selected from the group consisting of toluene, DMF, acetonitrile and cyclohexane. Preferably, the organic solvent is toluene.

The 1,2,4-triazole is 1,2,4-triazole or a salt thereof, for example an alkali metal salt. Optionally, the 1,2,4-triazole is the sodium salt of 1,2,4-triazole.

The organic solvent used in the step of purifying anastrozole may be a water immiscible solvent or a mixture of water immiscible solvents. Surprisingly, it has been found that a mixture of ethylacetate and diisopropylether is particularly preferred for the isolation and purification of anastrozole. This combination of solvents is particularly effective in aiding the removal of impurities, especially those formed during the bromination step.

Thus, according to another aspect of the present invention, there is provided a process for the preparation of anastrozole which comprises: a) brominating 3,5-bis(2-cyanoprop-2-yl)toluene (II) in an organic solvent using a brominating agent to obtain 3,5-bis(2-cyanoprop-2-yl)benzylbromide (III); b) isolating and purifying the bromo intermediate (III) using an organic solvent; c) alkylating the bromo intermediate in the presence of a base, optionally a phase transfer catalyst, a 1,2,4-triazole and an organic solvent to obtain anastrozole; d) isolating and purifying the anastrozole from ethylacetate and diisopropylether. Preferably, the organic solvent in the brominating step is acetonitrile. Preferably, the bromination reaction mass is heated to the reflux temperature of the organic solvent for a period of time no longer than 3 hours.

Furthermore, according to another aspect of the present invention, there is provided a process for purifying crude anastrozole comprising crystallising anastrozole from ethylacetate and diisopropylether. Suitably, the ethylacetate and diisopropylether are charged to the crude anastrozole, the mixture is optionally stirred for example for a period of time ranging from 10 minutes to 1 hour, suitably for around 30 minutes, chilling the mixture for example to a temperature ranging from about 0 to about 10° C., suitably from about 0 to about 5° C., and isolating the solid product, for example by filtration, washing and drying under vacuum.

In an embodiment, none of the organic solvents used in any of the steps is carbon tetrachloride.

In an embodiment, benzoyl peroxide is present in the bromination step.

In another embodiment, an acid is present in the bromination step. The acid may be sulphuric acid or acetic acid. Preferably, the acid is sulphuric acid. When an acid is present in the bromination step, the refluxing of the bromination reaction mass may be carried out in a shorter time, for example in one hour. This shorter time is particularly preferred as it aids in reducing the formation of impurity (IV).

Thus, a particularly preferred embodiment of the process for the preparation of anastrozole according to the present invention is one in which the organic solvent used in the brominating step is acetonitrile, the bromination reaction mass is heated to the reflux temperature of the organic solvent for a period of time no longer than 3 hours, the brominating agent is N-bromosuccinimide, an acid is optionally present during the bromination step, the organic solvent used in the purification of the brominated intermediate is a mixture of isopropyl alcohol and n-heptane, the organic solvent used in the alkylation step is toluene and the organic solvent used in the purification of anastrozole is a mixture of ethylacetate and diisopropylether.

In an embodiment, the purified product of the bromination reaction contains the impurity 3,5-bis(cyanoprop-2-yl)benzyl bromide (IV) in an amount ranging from 5 to 8%.

In a further embodiment, the purified product of step b) is substantially free from the impurity 3,5-bis(cyanoprop-2-yl)benzyl bromide (IV)

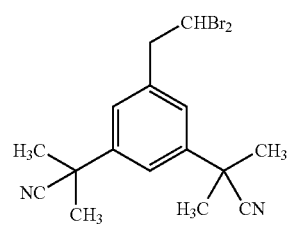

IV

The anastrozole prepared according to the process of the present invention may be obtained with purity greater than or equal to 99.8%. Typically, the anastrozole is obtained with purity of 99.8%. Desirably, the anastrozole is obtained with purity of 99.8%. Anastrozole prepared according to the process of the present invention forms another aspect of the present invention.

According to another aspect of the present invention, there is provided anastrazole having a purity greater than or equal to 99.8%. In an embodiment, the anastrozole has a purity of 99.8%. Preferably the anastrozole has a purity of 99.9%.

DETAILED DESCRIPTION OF THE INVENTION

In an embodiment, the process of the present invention is as shown in scheme III.

Scheme III

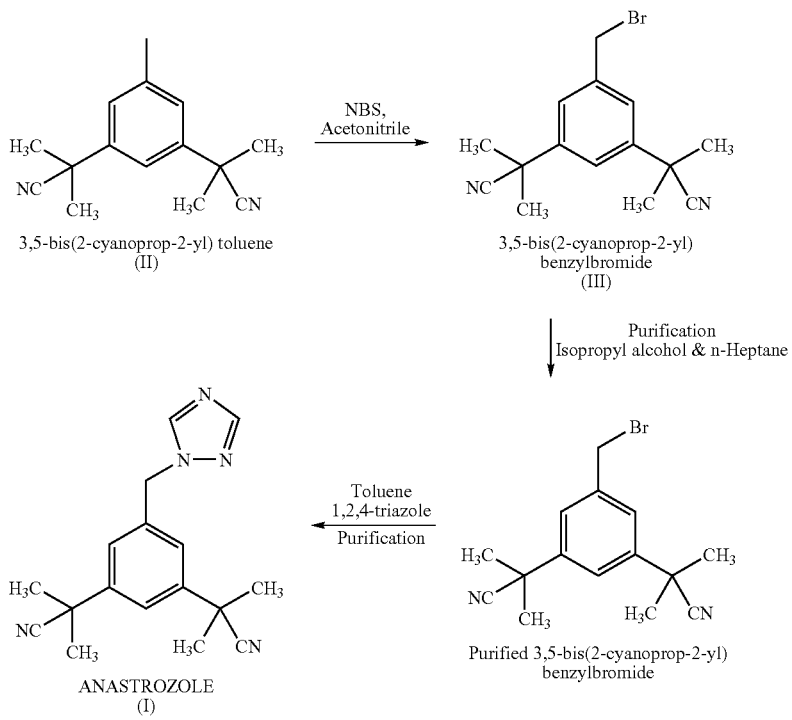

According to one embodiment of the present invention as depicted in scheme III, the starting material 3,5-bis(2-cyanoprop-2-yl)toluene (formula II), is brominated using N-bromosucccinimide (NBS) to the benzyl bromide intermediate 3,5-bis(2-cyanoprop-2-yl)benzylbromide (formula III) in the presence of benzoyl peroxide in acetonitrile.

The bromination reaction is carried out at reflux temperature for not more than 3 hours after which time the impurity 3,5-bis(cyanoprop-2-yl)benzylbromide, a compound of formula (IV), is formed in a substantially low percentage. In particular, impurity (IV) is formed in an amount ranging from about 5 to 8%. In U.S. Pat. No. '950, impurity (IV) is formed to an extent ranging from about 40 to 50% because of the solvent used and the longer reaction time.

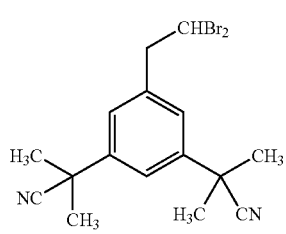

IV

Surprisingly it was found that when bromination is carried out in the presence of an acid such as sulphuric acid or acetic acid, the formation of the dibromo impurity IV is minimized and the reaction goes to completion in less than 1 hour. The product is formed in 110% w/w yield.

In another embodiment of the present invention, the small amount of the impurity of formula (IV) generated in the bromination step is efficiently removed by purifying the bromo intermediate using a suitable solvent, which results in 3,5-bis(cyanoprop-2-yl)benzyl bromide with purity greater than 90%. The suitable solvent used for purifying the bromo compound is an organic solvent and may be selected from the group consisting of isopropyl alcohol, n-heptane, n-hexane, toluene and mixtures thereof. A particularly preferred solvent is a mixture of isopropyl alcohol and n-heptane.

In yet another embodiment of the present invention, the purified bromo compound (formula (III)) is alkylated with 1,2,4-triazole in a suitable solvent using a suitable base in the presence of a phase transfer catalyst such as tetrabutyl ammonium bromide to obtain anastrozole, which is further purified using column chromatography, followed by precipitation/crystallization using ethyl acetate and diisopropyl ether to obtain pure anastrozole in high yield.

Suitable solvents used for the above alkylation reaction are selected from the group consisting of toluene, DMF, acetonitrile and cyclohexane, preferably toluene.

Suitable bases used are selected from the group consisting of potassium carbonate, sodium carbonate, sodium hydroxide, potassium hydroxide, sodium bicarbonate, potassium bicarbonate and mixtures thereof, preferably potassium carbonate and powdered potassium hydroxide.

The process of the present invention affords anastrozole in high yield and high purity, the purity of the pure anastrozole obtained may be measured by HPLC.

The anastrozole prepared by the present invention has purity greater than or equal to 99.8%. In particular, anastrozole prepared by the present invention may have purity of 99.9%.

EXAMPLES

The details of the invention are given in the following examples, which are provided for illustration only and therefore these should not be construed to limit the scope of the present invention in any manner.

Example 1

Preparation of 3,5-bis(2-cyanoprop-2-yl)benzyl bromide, compound of formula (III)

Acetonitrile (about 10 lts), 3,5-bis(2-cyanoprop-2-yl)toluene (1.0 kg), benzoyl peroxide (23 g) and sulphuric acid (10 g) were charged and heated to 50-55° C. To this N-bromosuccinimide (1000 g) was added over a period of 3 hours, maintained for 30 minutes, then the temperature was slowly raised to reflux (75-80° C.) and maintained for 1 hour. After reaction completion, the mass was cooled to 25-30° C., water (25 ml) was added and concentrated under vacuum to a residue at a temperature less than 60° C. The contents were cooled to 25-30° C., methylene choride (2500 ml) was charged, chilled to 10-15° C., the insolubles were filtered and washed with chilled methylene chloride (150 ml). The combined methylene chloride layer was washed with 10% sodium sulphite solution (300 ml), followed by washing with 10% sodium bicarbonate solution (300 ml) and 10% sodium chloride solution (300 ml). The methylene chloride layer was finally washed with water (300 ml), dried over sodium sulphate and concentrated to a residue under vacuum at 35-40° C. To this residue charged isopropyl alcohol followed by n-heptane, heated to 50-55° C., maintained for 30 minutes then slowly cooled to 25-30° C. and stirred for 1 hour. The material so obtained was filtered, washed with n-heptane (250 ml).

Purification:

Isopropyl alcohol (400 ml) and n-heptane (5 ltrs.) were charged to the above material, the contents were heated to 50-55° C., maintained for 30 minutes, cooled to 25-30° C., stirred for 1 hour at 25-30° C., filtered, washed with n-heptane (200 ml) and dried under vacuum at 35-40° C. to give 3,5-bis (2-cyanoprop-2-yl)benzyl bromide (1.1 kg, 110% yield (w/w), 81.6 mol % yield, 96% HPLC purity).

Example 2

Preparation of 3,5-bis(2-cyanoprop-2-yl)benzylbromide, compound of formula (III)

Acetonitrile (1300 ml), 3,5-bis(2-cyanoprop-2-yl)toluene (100 g), benzoyl peroxide (2.3 g) and acetic acid (1.2 ml) were heated to 50-55° C. To this, N-bromosuccinimide (100 g) was added over a period of 3 hours, maintained for 30 minutes, then the temperature was slowly raised to reflux (75-80° C.) and maintained for 3 hours. After reaction completion, the mass was cooled to 25-30° C., water (2.5 ml) was added and concentrated under vacuum to residue at a temperature lower than 60° C. The contents were cooled to 25-30° C., methylene chloride (250 ml) was charged, chilled to 10-15° C., and the insolubles were filtered and washed with chilled methylene chloride (15 ml). The combined methylene chloride layer was washed with 10% sodium sulphite solution (30 ml), followed by a wash with 10% sodium bicarbonate solution (30 ml) and 10% sodium chloride solution (30 ml). The methylene chloride layer was finally washed with water (30 ml), dried over sodium sulphate and concentrated to residue at 35-40° C. To this residue, isopropyl alcohol (30 ml) and n-heptane (490 ml) were charged, heated to 50-55° C., maintained for 30 minutes, slowly cooled to 25-30° C. and stirred for 1 hour. The material so obtained was filtered and washed with n-heptane (25 ml).

Purification:

To the above material, isopropyl alcohol (240 ml) and n-heptane (240 ml) were charged, the contents were heated to 55-60° C. for dissolution then allowed to cool to 40-44° C., filtered, washed with n-heptane (25 ml) and dried under vacuum at 35-40° C. to give 3,5-bis (2-cyanoprop-2-yl)benzyl bromide (81 g, 60 mol % yield, 95% HPLC purity).

Example 3

Preparation of 2,2'-[5-(1H-1,2,4-triazol-1-yl-methyl)-1,3-phenylene]-di(2-methyl propionitrile), compound of formula (I) [ANASTROZOLE]

Toluene (1000 ml), 1,2,4-triazole (27 g), potassium carbonate (110 g), powdered potassium hydroxide (20 g), tetrabutyl ammonium bromide (7 g) and 3,5-bis(2-cyanoprop-2-yl)benzyl bromide (100 g) were charged, heated to 85-90° C. and maintained for 5 hours. After reaction completion, the mass was cooled to 20-25° C., water (500 ml) was charged and the toluene layer was separated, the aqueous layer was extracted using toluene (300 ml), the toluene layer was combined, washed using water (500 ml) and the toluene layer dried over sodium sulphate. The toluene layer was concentrated under vacuum to residue at 50-55° C., isopropyl alcohol (18.8 ml) was charged followed by n-heptane (450 ml), the contents were stirred for 1 hour at 25-30° C., the contents were chilled to 0-5° C., maintained for 45 minutes, and the resulting material was filtered and washed with n-heptane (25 ml).

Purification:

The above material was loaded on a Silica gel column, eluted with methylene chloride followed by the polarity being increased (to an extent of 30%) using ethyl acetate. The pure fractions containing anastrozole were concentrated to residue at 40-45° C., cooled to 20-25° C., methanol (420 ml) was charged, stirred for dissolution, clarified over hyflo and concentrated to residue under vacuum at 40-45° C. The contents were cooled to 20-25° C., ethyl acetate (13.8 ml) followed by diisopropyl ether (445 ml) was charged, stirred for 30 minutes, chilled to 0-5° C., maintained for 30 minutes, filtered, washed with diisopropyl ether (50 ml) and dried under vacuum at 40-45° C. to give the title compound anastrozole (45 g, 47 mol. % yield, 99.9% HPLC purity).

It will be appreciated that the invention may be modified within the scope of the appended claims.

The invention claimed is:

1. A process for the preparation of anastrozole which comprises:

a) brominating 3,5-bis(2-cyanoprop-2-yl)toluene (II) in an organic solvent using a brominating agent to obtain 3,5-bis(2-cyanoprop-2-yl)benzylbromide (III);

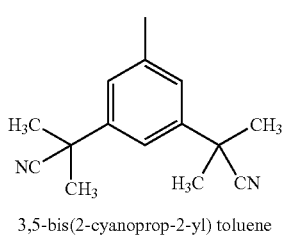

3,5-bis(2-cyanoprop-2-yl) toluene (II)

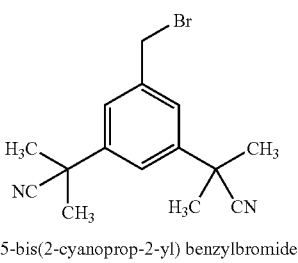

3,5-bis(2-cyanoprop-2-yl) benzylbromide (III)

b) heating the reaction mass of step a) to the reflux temperature of the organic solvent for a period of time no longer than 3 hours;
c) isolating and purifying the bromo intermediate (III) using an organic solvent;
d) alkylating the bromo intermediate in the presence of a base, optionally a phase transfer catalyst, a 1,2,4-triazole and an organic solvent to obtain anastrozole; and

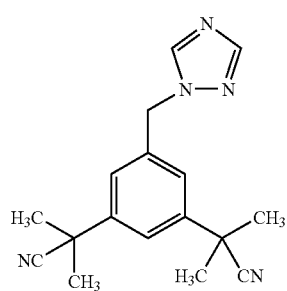

(I)

e) isolating and purifying the anastrozole from an organic solvent wherein an acid is present in step a).

2. The process according to claim 1, wherein the refluxing is carried out for 3 hours.

3. The process according to claim 1, wherein the refluxing is carried out for 1 hour.

4. The process according to claim 1, wherein the organic solvent used in step a) is acetonitrile.

5. The process according to claim 1, wherein the brominating agent is an N-halosuccinimide.

6. The process according to claim 5, wherein the N-halosuccinimide is N-bromosuccinimide.

7. The process according to claim 1, wherein the organic solvent used in step a) is acetonitrile and the brominating agent is N-bromosuccinimide.

8. The process according to claim 1, wherein the organic solvent used in step c) is selected from the group consisting of isopropyl alcohol, n-heptane, n-hexane, toluene and mixtures thereof.

9. The process according to claim 1, wherein the organic solvent used in step c) is a mixture of isopropyl alcohol and n-heptane.

10. The process according to claim 1, wherein the organic solvent used in step a) is acetonitrile, the brominating agent is N-bromosuccinimide and the organic solvent used in step c) is a mixture of isopropyl alcohol and n-heptane.

11. The process according to claim 1, wherein the organic solvent used in step d) is selected from the group consisting of toluene, DMF, acetonitrile and cyclohexane.

12. The process according to claim 1, wherein the organic solvent used in step d) is toluene.

13. The process according to claim 1, wherein the organic solvent used in step a) is acetonitrile, the brominating agent is N-bromosuccinimide, the organic solvent used in step c) is a mixture of isopropyl alcohol and n-heptane and the organic solvent used in step d) is toluene.

14. The process according to claim 1, wherein the base used in step d) is selected from the group consisting of potassium carbonate, sodium carbonate, sodium hydroxide, potassium hydroxide, sodium bicarbonate, potassium bicarbonate and mixtures thereof.

15. The process according to claim 1, wherein the base used in step d) is potassium carbonate and potassium hydroxide.

16. The process according to claim 15, wherein the potassium hydroxide is in powdered form.

17. The process according to claim 1, wherein, if present, the phase transfer catalyst is a tetraalkyl ammonium halide or a crown ether.

18. The process according to claim 17, wherein the tetraalkyl ammonium halide is tetrabutylammonium bromide.

19. The process according to claim 1, wherein the triazole used in step d) is 1,2,4-triazole or sodium triazole.

20. The process according to claim 1, wherein the organic solvent used in step e) is a water immiscible solvent.

21. The process according to claim 20, wherein the organic solvent used in step e) is a mixture of ethylacetate and diisopropylether.

22. The process according to claim 1, wherein the organic solvent used in step a) is acetonitrile, the brominating agent is N-bromosuccinimide, the organic solvent used in step c) is a mixture of isopropyl alcohol and n-heptane, the organic solvent used in step d) is toluene and the organic solvent used in step e) is a mixture of ethylacetate and diisopropylether.

23. The process according to claim 1, wherein none of the organic solvents is carbon tetrachloride.

24. The process according to claim 1, wherein benzoyl peroxide is present in step a).

25. A process for the preparation of anastrozole which comprises:
a) brominating 3,5-bis(2-cyanoprop-2-yl)toluene (II) in an organic solvent using a brominating agent to obtain 3,5-bis(2-cyanoprop-2-yl)benzylbromide (III);

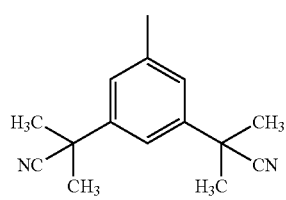

3,5-bis(2-cyanoprop-2-yl) toluene (II)

-continued

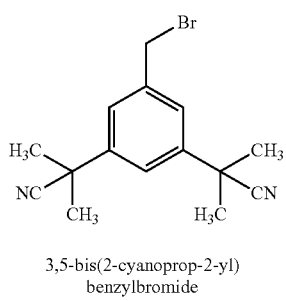

3,5-bis(2-cyanoprop-2-yl) benzylbromide (III)

b) heating the reaction mass of step to the reflux temperature of the organic solvent for a period of time no longer than 3 hours;
c) isolating and purifying the bromo intermediate (III) using an organic solvent;
d) alkylating the bromo intermediate in the presence of a base, optionally a phase transfer catalyst, a 1,2,4-triazole and an organic solvent to obtain anastrozole; and

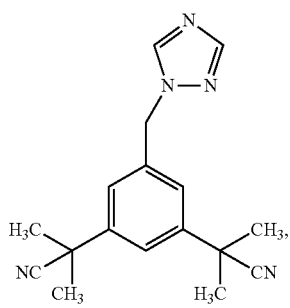

(I)

e) isolating and purifying the anastrozole from an organic solvent wherein an acid is present in step a) and, wherein the acid is sulphuric acid or acetic acid.

26. The process according to claim 25, wherein the acid is sulphuric acid.

27. The process according to claim 1, wherein the purified product of step c) is substantially free from 3,5-bis(cyanoprop-2-yl)benzyl bromide (IV)

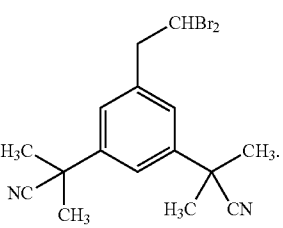

(IV)

28. The process according to claim 1, wherein the purified product of step c) contains 3,5-bis(cyanoprop-2-yl)benzyl bromide (IV) in an amount ranging from 5 to 8%.

29. The process according to claim 1, wherein the anastrozole in step e) is obtained with purity greater than 99.8%.

* * * * *

UNITED STATES PATENT AND TRADEMARK OFFICE
CERTIFICATE OF CORRECTION

| | | |
|---|---|---|
| PATENT NO. | : 7,989,636 B2 | |
| APPLICATION NO. | : 12/444613 | |
| DATED | : August 2, 2011 | |
| INVENTOR(S) | : Pathi et al. | |

It is certified that error appears in the above-identified patent and that said Letters Patent is hereby corrected as shown below:

Column 15, Line 15, replace   "mass of step to the reflux" with   -- mass of step a) to the reflux --

Signed and Sealed this
Twenty-seventh Day of September, 2011

David J. Kappos
*Director of the United States Patent and Trademark Office*